US011844653B2

(12) United States Patent
Igarashi et al.

(10) Patent No.: US 11,844,653 B2
(45) Date of Patent: Dec. 19, 2023

(54) PROBE AND ULTRASOUND DIAGNOSTIC DEVICE USING THE SAME

(71) Applicant: FUJIFILM Healthcare Corporation, Kashiwa (JP)

(72) Inventors: Yutaka Igarashi, Chiba (JP); Shinya Kajiyama, Chiba (JP); Kengo Imagawa, Chiba (JP); Yoshihiro Hayashi, Chiba (JP)

(73) Assignee: FUJIFILM Healthcare Corporation, Chiba (JP)

( * ) Notice: Subject to any disclaimer, the term of this patent is extended or adjusted under 35 U.S.C. 154(b) by 99 days.

(21) Appl. No.: 17/745,107

(22) Filed: May 16, 2022

(65) Prior Publication Data
US 2022/0386997 A1 Dec. 8, 2022

(30) Foreign Application Priority Data
Jun. 4, 2021 (JP) ................. 2021-094700

(51) Int. Cl.
*A61B 8/00* (2006.01)
*A61B 8/08* (2006.01)

(52) U.S. Cl.
CPC .................. *A61B 8/5207* (2013.01)

(58) Field of Classification Search
CPC ................. A61B 8/5207; A61B 8/00
(Continued)

(56) References Cited

U.S. PATENT DOCUMENTS 8,226,563 B2 * 7/2012 Peteresen ............. G01S 7/5208
600/443

FOREIGN PATENT DOCUMENTS

| JP | 2013-188421 | 9/2013 |
|---|---|---|
| JP | 2020-081451 | 6/2020 |

OTHER PUBLICATIONS

S. Kajiyama et al., T/R-Switch Composed of 3 High-Voltage MOSFETs with 12.1 μW Consumption that can Perform Per-channel TX to RX Self-Loopback AC Tests for 3D.
(Continued)

*Primary Examiner* — Tomi Skibinski
(74) *Attorney, Agent, or Firm* — Paul Teng (57) ABSTRACT

To provide a probe including a TGC circuit therein. The probe includes a plurality of receive circuits. Each receive circuit includes: an ultrasound transducer; a transmit/receive switch; a variable attenuator; a first capacitor; and an amplifier. The ultrasound transducer converts the receive signal into a ground level electric signal and outputs the ground level electric signal as a first output signal. The transmit/receive switch is connected to a first signal line, and switches depending on whether to output the first output signal output from the ultrasound transducer to the first signal line. The variable attenuator includes a control terminal and two terminals, and changes a resistance value between the two terminals other than the control terminal based on a control signal input to the control terminal. The amplifier has an input terminal connected to the first capacitor and includes at least an amplifier circuit configured to amplify an electric signal of the first signal line and output the amplified electric signal to a second signal line. In the variable attenuator, one of the two terminals other than the control terminal is connected to the first signal line, and the other terminal is connected to the ground via a second capacitor different from the first capacitor.

14 Claims, 8 Drawing Sheets

(58) Field of Classification Search
USPC .......................................................... 327/306
See application file for complete search history.

(56) References Cited

OTHER PUBLICATIONS

Ultrasound Imaging with 3072-channel Transceiver, IEEE Asian Solid-State Circuits Conf. Proc. Tech. Papers, pp. 305-308, Nov. 2019.

* cited by examiner

PROBE AND ULTRASOUND DIAGNOSTIC DEVICE USING THE SAME

BACKGROUND OF THE INVENTION

1. Field of the Invention

The present invention relates to a probe suitable for an ultrasound diagnostic apparatus and an ultrasound diagnostic apparatus.

2. Description of the Related Art

In recent years, in order to obtain a three-dimensional (3D) image with an ultrasound diagnostic apparatus, a 2D array probe in which ultrasound transducers are two-dimensionally arranged has been developed. While several thousands to ten thousands of ultrasound transducers are mounted on the 2D array probe, the number of signal lines in a cable connecting the probe and a main body of the ultrasound diagnostic apparatus is limited to about 200. Therefore, in the related art, JP-A-2020-81451 and Non-Patent Literature 1 (Kajiyama, S.; Igarashi, Y.; Yazaki, T.; Katsube, Y.; Nishimoto, T.; Nakagawa, T.; Nakamura, Y.; Hayashi, Y.; Yamawaki, T., "T/R-Switch Composed of 3 High-Voltage MOSFETs with 12.1 µW Consumption That Can Perform Per-Channel TX to RX Self-Loopback AC Tests for 3D Ultrasound Imaging with 3072-Channel Transceiver", IEEE Asian Solid-State Circuits Conference Proceedings of Technical Papers, pp. 305-308, November 2019.) disclose a configuration in which receive beamforming executed in a main body of an ultrasound diagnostic apparatus is divided into two stages, a first stage receive beamforming is executed by an integrated circuit (IC) disposed in a probe, and a signal after the first stage receive beamforming is output from the probe to the ultrasound diagnostic apparatus. In the IC disclosed in JP-A-2020-81451 and Non-Patent Literature 1, ultrasound transducers and transmit and receive circuits of the same number as the ultrasound transducers are integrated, a transmit/receive switch, an amplifier, and a delay circuit are provided in a receive circuit, and amplified receive signals are added after being delayed.

In general, since a probe of an ultrasound diagnostic apparatus is a system that transmits an ultrasound wave by itself and receives a reflected wave thereof, the probe receives an ultrasound wave having a strong sound pressure due to reflection from a bone or the like at the time of acquiring an image of a portion near a body surface, and receives an ultrasound wave having a low sound pressure attenuated by propagating through a human body at the time of acquiring an image of a portion far (deep) from the body surface. Therefore, in a normal ultrasound diagnostic apparatus that is not a 2D array probe, a circuit called time gain control (hereinafter, also referred to as "TGC") that increases an amplification gain of a receive signal in accordance with the passage of time from the start of receive is provided in the main body of the ultrasound diagnostic apparatus.

For example, in an ultrasound diagnostic apparatus disclosed in JP-A-2013-188421, an ultrasound wave is transmitted from the probe into a subject, the probe receives an ultrasound wave reflected in the subject, and a receive unit in a main body of the ultrasound diagnostic apparatus processes an obtained receive signal. The receive unit is configured to prevent the transmit signal from going around to the receive unit by a transmit/receive switch unit, and to amplify the receive signal received through the transmit/receive switch unit by an amplification unit. A variable attenuation unit for attenuating the receive signal is disposed between the transmit/receive switch unit and the amplification unit. The transmit/receive switch unit is implemented by a diode bridge. The variable attenuation unit is configured such that two sets of circuits in which a resistor, a diode, and a variable bias voltage source are sequentially connected in series are connected in parallel, an end portion on the resistor side is connected to a signal line through which a receive signal flows, and an end portion on the variable bias voltage source side is connected to the ground. In a case of a receive signal having a large signal amplitude reflected near the body surface, a bias voltage of the variable bias voltage source is set such that the diode is turned on, and the receive signal is attenuated by resistance voltage division. In a case of a receive signal having a small signal amplitude reflected at a deep region of the subject, the bias voltage of the variable bias voltage source is adjusted, and the diode is turned off. As a result, an attenuation degree is changed from large to small with the passage of a receive time.

U.S. Pat. No. 8,226,563 discloses that in a receive circuit of an ultrasound image, a gain of an amplifier is made variable by changing a bias current of a preamplifier connected to a transducer element or by adjusting a feedback amount of a differential output amplifier provided at a subsequent stage of the preamplifier (FIGS. 3 and 4 of U.S. Pat. No. 8,226,563).

SUMMARY OF THE INVENTION

Receive circuits arranged in the 2D array probes disclosed in JP-A-2020-81451 and Non-Patent Literature 1 do not include a circuit for executing time gain control.

On the other hand, since circuits for executing the time gain control disclosed in JP-A-2013-188421 and U.S. Pat. No. 8,226,563 are all circuits arranged in a main body of an ultrasound diagnostic apparatus, the circuits cannot be mounted as they are in a minute integrated circuit in the 2D array probe from any viewpoint of space, power consumption, and circuit configuration.

Specifically, in the ultrasound diagnostic apparatus disclosed in JP-A-2013-188421, a control signal for controlling a voltage of a bias voltage source is required for a variable attenuation unit for implementing the time gain control, but generation of the control signal needs to be executed by an external circuit. Even if the variable attenuation unit can be mounted on the IC in the probe, since the external circuit for generating the control signal is disposed in the main body of the ultrasound diagnostic apparatus, a signal line for transmitting the generated control signal to the inside of the probe is required. However, the number of the signal lines for connecting the probe and the main body of the ultrasound diagnostic apparatus is limited.

Although a diode is used in the variable attenuation unit of JP-A-2013-188421, the diode has a large driving power, and even if the variable attenuation unit can be mounted on the IC in the probe, it is necessary to supply a large driving power to the IC in the probe, which leads to an increase in temperature of the probe. There is also a problem that the diode has a large variation in performance and a variation in attenuation degree of a variable attenuator becomes large.

Furthermore, in the receive circuit of JP-A-2013-188421, the transmit/receive switch is implemented by a diode bridge, but the diode bridge easily causes fluctuation in the receive signal output at the time of switching.

On the other hand, in an ultrasound device of U.S. Pat. No. 8,226,563, TGC is executed using a preamplifier, a bias current is variable, and a gain variable function is implemented by using a current feedback type in which a MOSFET is used as a resistor. However, a gain variable width that can be generated by varying the bias current is small. When a current value is small, distortion becomes large. In a case of the current feedback type in which MOSFET is used as a resistor, a process dependence of the gain increases.

In the 2D array probe, a low noise amplifier circuit (hereinafter, referred to as LNA) having an independent gain variable function is required for each ultrasound transducer array of several thousands to ten thousand elements. In the circuit configuration of the receive circuit disclosed in JP-A-2013-188421 and U.S. Pat. No. 8,226,563, it is difficult to minimize the variation in the gain of each LNA while providing a gain variable function (30 dB or more) necessary for several thousands to ten thousand LNAs. Therefore, it is impossible to implement a configuration in which a gain control signal is supplied to a large number of LNA groups mounted on an integrated circuit and TGC control is executed without increasing an area of each LNA.

Inventors have found that in the circuit configuration of the receive circuit mounted in the probe disclosed in JP-A-2020-81451 and Non-Patent Literature 1, a bias potential of the signal line for transmitting the receive signal to the amplifier circuit varies between an OFF state (at the time of transmitting) and an ON state (at the time of receiving) of the transmit/receive switch. Therefore, when an attenuation circuit for time gain control is disposed at a front stage of the amplifier circuit, the receive signal is affected by fluctuation of the bias potential.

An object of the invention is to solve the above-described problem and to provide a probe including a TGC circuit therein.

In order to solve the above-mentioned problem, an example of the probe of the invention is a probe that is connected to an ultrasound diagnostic apparatus, transmits an ultrasound wave to a diagnostic site, and receives a receive signal that is a reflected wave. The probe includes a plurality of receive circuits.

Each receive circuit includes: an ultrasound transducer; a transmit/receive switch; a variable attenuator; a first capacitor; and an amplifier.

The ultrasound transducer converts the receive signal into a ground level electric signal and outputs the ground level electric signal as a first output signal.

The transmit/receive switch is connected to a first signal line, and switches depending on whether to output the first output signal output from the ultrasound transducer to the first signal line.

The variable attenuator includes a control terminal and two terminals, and changes a resistance value between the two terminals other than the control terminal based on a control signal input to the control terminal.

The first capacitor is connected to the first signal line.

The amplifier has an input terminal connected to the first capacitor and includes at least an amplifier circuit configured to amplify an electric signal of the first signal line and output the amplified electric signal to a second signal line.

The transmit/receive switch outputs a bias potential to the first signal line when the transmit/receive switch is turned off.

In the variable attenuator, one of the two terminals other than the control terminal is connected to the first signal line, and the other terminal is connected to the ground via a second capacitor different from the first capacitor.

According to the invention, it is possible to provide the probe including a TGC circuit therein.

Problems, configurations, and effects other than those described above will be clarified based on the following descriptions of embodiments.

DESCRIPTION OF EMBODIMENTS

Hereinafter, embodiments of the invention will be described with reference to the drawings. In the drawings for illustrating the embodiments, the same components are denoted by the same names and reference numerals, and repeated description thereof will be omitted.

Notations such as "first", "second", and "third" in the present specification and the like are given to identify components, and do not necessarily limit the number or order. A number for identifying a component is used for each context, and a number used in one context does not necessarily indicate the same configuration in other contexts. A component identified by a certain number does not interfere with the function of a component identified by another number.

First Embodiment

Figure 1:
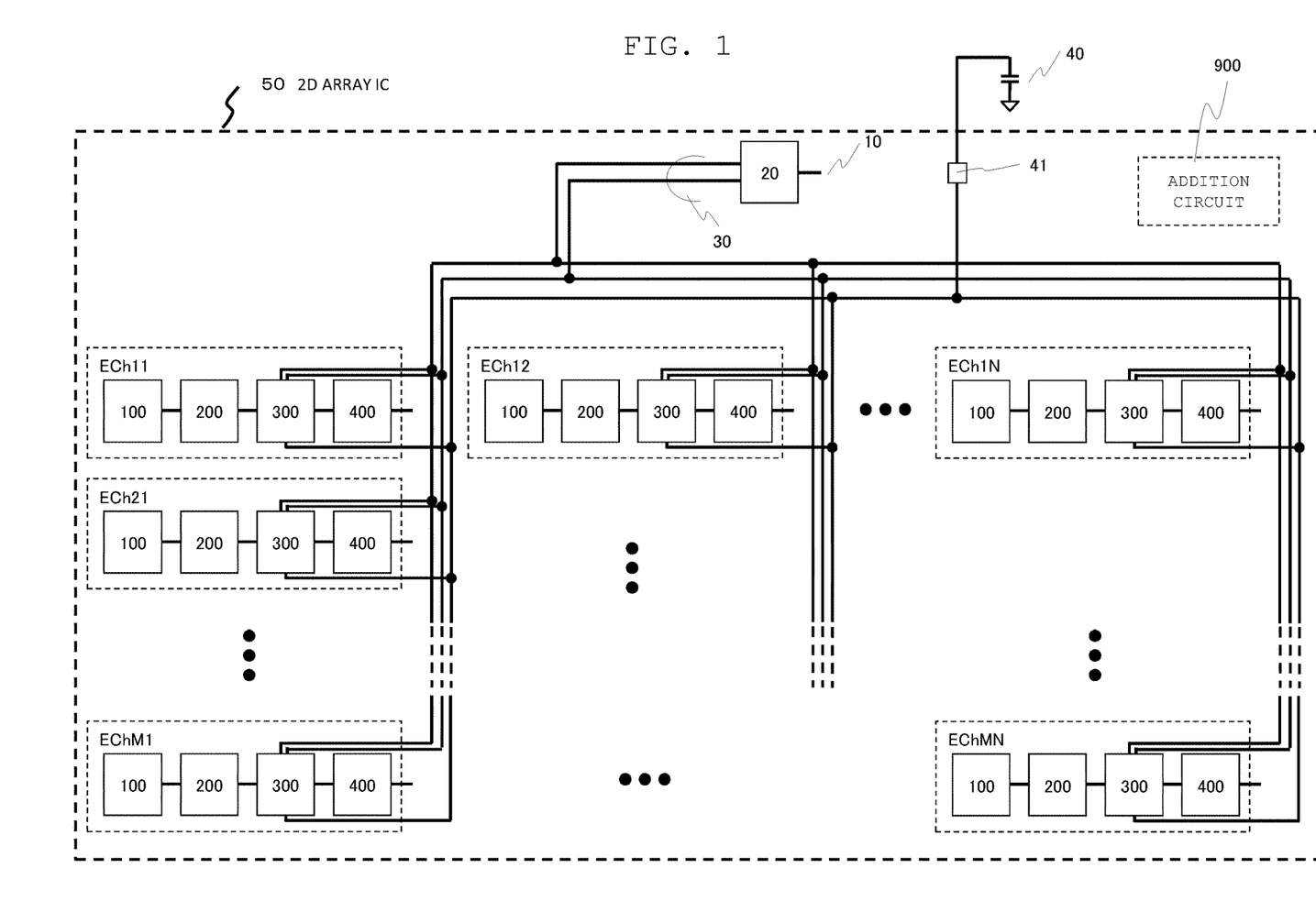
FIG. 1 is a block diagram showing an outline of an integrated circuit (2D array IC 50) in which a plurality of transmit and receive circuits (transmit and receive channels ECHs) are mounted, in a probe according to a first embodiment.
Figure 2:
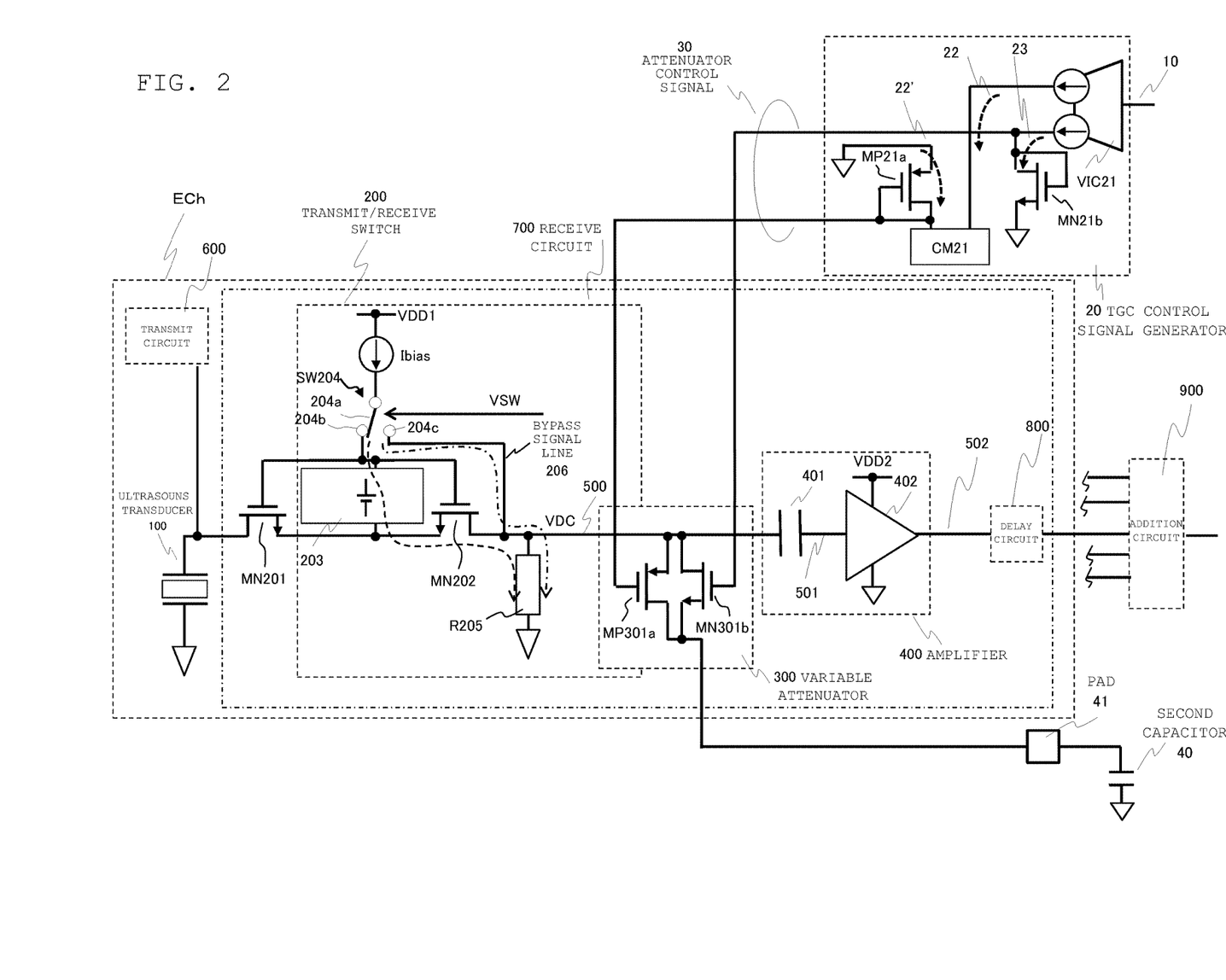
FIG. 2 is a block diagram showing a configuration of one transmit and receive circuit (a transmit and receive channel ECh) in the probe according to the first embodiment.

A probe for an ultrasound diagnostic apparatus according to a first embodiment will be described with reference to the drawings. FIG. 1 is a diagram showing an outline of an integrated circuit (a 2D array IC 50) in which a plurality of transmit and receive circuits (transmit and receive channels ECHs) in a probe are mounted, and FIG. 2 is a diagram showing a configuration of one transmit and receive circuit (a transmit and receive channel ECh).

Outline of Probe

An ultrasound probe according to the first embodiment is connected to the ultrasound diagnostic apparatus, transmits an ultrasound wave to a target site of a subject, and receives an ultrasound signal that is a reflected wave.

Ultrasound transducers 100 that are arranged two-dimensionally (2D) are mounted on the probe. The number of the ultrasound transducers is, for example, several thousands to ten thousands.

As shown in FIGS. 1 and 2, the probe includes: a plurality of ultrasound transducers 100; a plurality of transmit circuits 600 that output transmit signals to the ultrasound transducers 100, respectively; a plurality of receive circuits 700 that execute processing such as time gain control on receive signals of the ultrasound transducers 100 and then delay the receive signals; an addition circuit 900 that adds outputs of the plurality of receive circuits 700; and a TGC control signal generator 20.

The ultrasound transducers 100, the transmit circuits 600, the receive circuits 700, and the addition circuit 900 are integrated on the 2D array IC 50.

Each circuit of the 2D array IC 50 executes time gain control processing and amplification processing on the receive signals output from the ultrasound transducers 100, executes receive beamforming (delay addition in this case) of a first stage, and bundles the receive signals for each sub channel (hereinafter, also referred to as SCh). The number of signals of the bundled sub channels is equal to or less than the number of signal lines (for example, about 200) in a cable connecting the probe and the main body of the ultrasound diagnostic apparatus, and the signals are input to the main body of the ultrasound diagnostic apparatus by being transmitted by the signal lines.

The main body of the ultrasound diagnostic apparatus executes receive beamforming in a second stage by a circuit therein, focuses on a receive focal point for each depth on a receive scanning line set in the subject, and generates a signal after phasing addition.

The main body of the ultrasound diagnostic apparatus generates a tomographic image and a 3D volume data of the subject by using the signal after the phasing addition.

Circuit in Probe

A circuit in the probe will be specifically described with reference to FIGS. 1 and 2.

As described above, the plurality of ultrasound transducers 100, the plurality of transmit circuits 600, and the plurality of receive circuits 700 are arranged in the probe.

As shown in FIG. 2, one ultrasound transducer 100, one transmit circuit 600, and one receive circuit 700 form a transmit and receive channel (Element Channel) ECh. A plurality of (M×N) transmit and receive channels ECh11 to EChMN are arranged and mounted in a two-dimensional matrix on the 2D array IC 50. The M×N transmit and receive channels ECh11 to EChMN are all circuits designed with the same circuit constant.

Each of the receive circuits 700 includes: a transmit/receive switch 200; a variable attenuator 300 that executes time gain control; an amplifier 400; and a delay circuit 800. The transmit/receive switch 200 and the amplifier 400 are connected by a first signal line 500. The variable attenuator 300 is connected to an intermediate portion of the first signal line 500. The delay circuit 800 is connected to a second signal line 502 of an output of the amplifier 400. The delay circuit 800 is also connected to the transmit circuit 600, and also executes delay processing of the transmit signal.

Ultrasound Transducer

At the time of transmitting, the ultrasound transducer 100 receives a transmit signal from the transmit circuit 600, converts the transmit signal into an ultrasound signal, and transmits the ultrasound signal to the subject. At the time of receive, the ultrasound transducer 100 converts the ultrasound signal reflected from the subject into a ground level electric signal, and outputs the electric signal to the transmit/receive switch 200 as a first output signal.

Transmit/Receive Switch 200

The transmit/receive switch 200 is a switch that switches depending on whether to output the first output signal from the ultrasound transducer 100 to the first signal line 500. At the time of transmitting, the transmit/receive switch 200 is switched off to protect the receive circuit 700 in the subsequent stage from a transmit signal having a large amplitude output from the transmit circuit 600 to the ultrasound transducer 100.

The transmit/receive switch 200 includes: one or more transmit/receive switch high-breakdown-voltage MOSFETs (MN201 and MN202 of N-channel MOSFETs); a floating voltage generation unit 203; a switch element (SW) 204; a resistor R205; and a bypass signal line 206.

Sources and gates of MN201 and MN202 of the transmit/receive switch MOSFETs are connected to each other. A drain of MN201, which is one MOSFET of the transmit/receive switch 200, is connected to the ultrasound transducer 100, and a drain of MN202, which is another MOSFET, is connected to the first signal line 500.

The floating voltage generation unit 203 is, for example, a circuit as shown in FIG. 4 of Non-Patent Literature 1, and generates a voltage to be applied between the gates and sources of the MN201 and the MN202.

The switch element 204 includes: a switch terminal 204a connected to a power supply VDD1; an ON terminal 204b; and an OFF terminal 204c.

The ON terminal 204b is connected to the floating voltage generation unit 203. In an ON state when the switch terminal 204a is connected to the ON terminal 204b side (at the time of receive of the ultrasound wave), the switch element 204 supplies a bias current Ibias to the floating voltage generation unit.

On the other hand, the OFF terminal 204c is connected to the first signal line 500 by the bypass signal line 206. In an OFF state when the switch terminal 204a is connected to the OFF terminal 204c (at the time of transmitting of the ultrasound wave), the bias current Ibias is caused to directly flow into the first signal line 500.

Accordingly, the transmit/receive switch 200 can switch depending on whether to output the first output signal from the ultrasound transducer 100 to the first signal line 500.

When the switch element 204 is turned on, the bias current Ibias flows from the resistor R205 to the ground via the floating voltage generation unit 203 and the MN202. On the other hand, when the switch element 204 is turned off, the bias current Ibias flows from the resistor R205 to the ground via the bypass signal line 206. Therefore, since the bias current Ibias always flows through the resistor R205, a potential of the first signal line 500 becomes a potential determined by a product of the resistor R205 and the bias current Ibias. In other words, the transmit/receive switch 200 outputs a bias potential to the first signal line 500 when the transmit/receive switch 200 is turned off. Moreover, the bias potential output to the first signal line 500 when the transmit/receive switch 200 is turned off is equal to a bias potential output to the first signal line 500 when the transmit/receive switch 200 is turned on. Therefore, since the potential of the first signal line 500 can be kept constant regardless of whether the transmit/receive switch 200 is turned on or off, by designing a capacitance of the first capacitor 401 in the amplifier 400, an operation of a low noise amplifier circuit (hereinafter, referred to as LNA) 402 in the amplifier 400 can be stabilized. The capacitance of the first capacitor 401 in the amplifier 400 will be described in detail later.

Variable Attenuator

The variable attenuator 300 attenuates the receive signal input from the ultrasound transducer 100 to the first signal line 500 via the transmit/receive switch 200, and implements time gain control. Specifically, the variable attenuator 300 executes processing in which the receive signal of the ultrasound wave reflected near the body surface of the subject, which is input to the first signal line 500 at the start of the receive, is greatly attenuated, and the receive signal of the ultrasound wave reflected at the deep region of the subject with the passage of time is not attenuated.

The variable attenuator 300 includes an element having a control terminal and two terminals. According to the present embodiment, an MP301*a* of a P-channel MOSFET and an MN301*b* of an N-channel MOSFET are used as elements, and these elements are connected in parallel to form the variable attenuator 300.

One end of the MP301*a* and MN301*b* connected in parallel is connected to the first signal line 500. The other end of the MP301*a* and MN301*b* connected in parallel is connected to a pad 41 provided in the 2D array IC 50. One terminal of a second capacitor 40 is connected to the pad 41, and the other terminal of the second capacitor 40 is grounded.

As a result, a resistance value between the two terminals (source and drain) other than the control terminal changes according to an attenuator control signal 30 input from the TGC control signal generator 20 to the control terminal (gate). Specifically, the variable attenuator 300 can attenuate the signal of the first signal line 500 by combining a variably controlled resistance value of the variable attenuator, an impedance of the ultrasound transducer 100, and an ON resistance of the transmit/receive switch 200.

Therefore, by changing the attenuator control signal 30 input to the variable attenuator 300 in accordance with the passage of time from the transmitting (or the start of receive), an attenuation rate of the variable attenuator 300 can be changed, and the time gain control can be implemented.

As shown in FIG. 1, the second capacitor (a common capacitor) 40 is commonly connected to the variable attenuators 300 of all the transmit and receive channels ECh11 to EChMN.

As a capacitance of the second capacitor 40 increases, a lowest frequency of a frequency band that can be attenuated by the variable attenuator 300 can be reduced. Therefore, a value of an electrostatic capacitance of the second capacitor 40 is designed in advance such that the entire desired frequency band can be attenuated by the variable attenuator 300.

The second capacitor 40 requires an impedance sufficiently smaller than the variably controlled resistance value of the variable attenuator 300, the impedance of the ultrasound transducer 100, and the ON resistance of the transmit/receive switch 200, which are disposed in each of the transmit and receive channels ECh11 to EChMN. On the other hand, the first capacitor 401 forms a high-pass filter in combination with an input impedance of the LNA 402, and a cutoff frequency thereof is determined by a product of a large input impedance of the LNA 402 and a capacitance of the first capacitor 401. The impedance of the ultrasound transducer 100 is several kiloohms, and the ON resistance of the transmit/receive switch 200 is several tens to several hundreds ohms, whereas the large input impedance of the LNA 402 is several hundreds to several megaohms, and a receive band is determined by a combination of the large impedance having a different digit and the capacitance of the first capacitor 401, and therefore, an electrostatic capacitance value of the second capacitor 40 is larger than an electrostatic capacitance value of the first capacitor 401.

A principle of implementing time gain control by the variable attenuator 300 and a design of the value of the electrostatic capacitance $C_{40}$ of the second capacitor 40 will be described in detail later using mathematical expressions.

The second capacitor 40 also functions to prevent the bias current Ibias of the transmit/receive switch 200 from flowing into the variable attenuator 300 via the first signal line 500.

TGC Control Signal Generator 20

The TGC control signal generator 20 generates a control signal for the variable attenuator 300. The TGC control signal generator 20 is a circuit that receives the TGC control signal 10 and generates a control signal to be input to the gates of the MP301*a* and the MN301*b* of the variable attenuator 300. The TGC control signal 10 can be generated by the ultrasound diagnostic apparatus, or can be generated by the 2D array IC 50.

As shown in FIG. 1, the TGC control signal generator 20 is mounted in a region around a region where a plurality of receive circuits are mounted on the 2D array IC 50.

As described above, according to the present embodiment, it is possible to implement both the variable attenuator 300 that implements the TGC on the 2D array IC 50 and the TGC control signal generator 20 that generates the control signal for the variable attenuator 300.

The TGC control signal generator 20 includes: a voltage-current converter VIC21; a current mirror CM21; an MN21*b* which is an N-channel MOSFET; and an MP21*a* which is a P-channel MOSFET. Details of the circuit configuration will be described later.

Amplifier 400

The amplifier 400 includes the LNA 402. The amplifier 400 amplifies the receive signal attenuated by the variable attenuator 300. According to the present embodiment, since the variable attenuator 300 can attenuate a large-amplitude signal reflected near the body surface of the subject, a gain of the LNA 402 can be set to be large in accordance with a signal having a small amplitude reflected at a deep portion of the subject. Therefore, an amplitude of the receive signal from the deep portion can be greatly amplified, and accuracy of the image can be improved.

The first capacitor 401 is inserted in series in the first signal line 500 between the LNA 402 and the transmit/receive switch. That is, the LNA 402 receives the signal of the first signal line 500 via the first capacitor 401, amplifies the signal, and outputs the amplified signal to the second signal line 502.

The first capacitor 401 holds, as a direct-current voltage, a difference between the potential of the first signal line 500 determined by the product of the resistor R205 and the bias current Ibias and a potential suitable for an operation of the LNA 402. Therefore, the capacitance of the first capacitor 401 is designed in advance according to the difference between the potential suitable for the operation of the LNA 402 and the potential of the first signal line 500.

The first capacitor 401 is preferably inserted in the first signal line 500 between the variable attenuator 300 and the LNA 402, but the variable attenuator 300 may be inserted between the first capacitor 401 and the LNA 402.

Operation of Each Unit During Transmit and Receive

Operations of the circuit on the 2D array IC 50 of the probe at the time of transmit and receive will be described.

The transmit and receive channels ECh11 to EChMN are divided into a plurality of sub channels (SCh) in advance.

Transmitting

At the time of transmitting, a transmit signal generated by the main body of the ultrasound diagnostic apparatus or the 2D array IC is branched into circuits of all transmit and receive channels EChs in one sub channel. The delay circuit 800 of each transmit and receive channel ECh gives a predetermined delay amount to the transmit signal. The transmit circuit 600 amplifies the delayed transmit signal and outputs the amplified transmit signal to the ultrasound transducer 100.

Each ultrasound transducer 100 converts a transmit signal delayed by a predetermined amount into an ultrasound wave and transmits the ultrasound wave to the subject. As a result, an ultrasound wave having a predetermined transmit focal point is transmitted.

At the time of transmitting, the transmit/receive switch 200 of the receive circuit 700 switches the switch element (SW) 204 such that the switch terminal 204a is switched to the OFF terminal 204c side by a control signal VSW.

As a result, the bias current Ibias flows to the first signal line 500 side of the transmit/receive switch 200 through the bypass signal line 206, and flows to the ground through the resistor R205.

Therefore, since the bias current Ibias does not flow to the floating voltage generation unit 203, gate-source voltages of the MN201 and the MN202 become voltages smaller than a threshold value, and the transmit/receive switch 200 is turned off.

Therefore, the transmit/receive switch 200 can protect the receive circuit 700 in the subsequent stage from the transmit signal having a large amplitude output from the transmit circuit 600 to the ultrasound transducer 100.

At this time, the bias current Ibias of the transmit/receive switch 200 is supplied to the first signal line 500 through the bypass signal line 206.

Therefore, the potential of the first signal line 500 at the time of transmitting is VDC determined by the product of the bias current Ibias and the resistance value of the resistor R205.

Receiving

The ultrasound wave transmitted to the subject is reflected by tissue or the like in the subject while propagating in the subject, and reaches the ultrasound transducer 100 again.

The ultrasound transducer 100 receives a reflected wave of the ultrasound wave, converts the reflected wave into an electric signal, and outputs a receive signal.

The transmit/receive switch 200 switches the bias current Ibias using the SW in response to a command of the control signal VSW. At the time of receiving, the bias current Ibias is caused to flow to the floating voltage generation unit 203 to generate the gate-source voltages for turning on the MN201 and the MN202 which are high-breakdown-voltages Nch MOSFETs. As a result, the transmit/receive switch 200 is turned on.

As a result, the receive signal output from the ultrasound transducer 100 is applied to the first signal line 500, and oscillates around the potential of the first signal line 500.

The bias current Ibias that passes through the floating voltage generation unit 203 flows to the ground via the MN202 and the resistor R205.

Therefore, the potential of the first signal line 500 at the time of receiving is VDC determined by the product of the bias current Ibias for operating the floating voltage generation unit 203 and the resistance value of the resistor R205.

The receive signal output from the ultrasound transducer 100 oscillates around the potential VDC of the first signal line 500 in the first signal line 500.

As described above, according to the present embodiment, the bias current Ibias is configured to be connected to the ground via the resistor R205 even when the transmit/receive switch 200 is switched between the OFF state and the ON state at the time of transmit and receive. In this way, the potential of the first signal line 500 can be kept constant without being changed by switching between transmit and receive.

The receive signal of the first signal line 500 is input to the variable attenuator 300.

The variable attenuator 300 attenuates the electric signal according to a level of the attenuator control signal 30.

The attenuator control signal 30 is a pair of signals generated by the TGC control signal generator 20 based on the TGC control signal 10, and is input to the control terminal (gate) of the variable attenuator 300.

Figure 3:
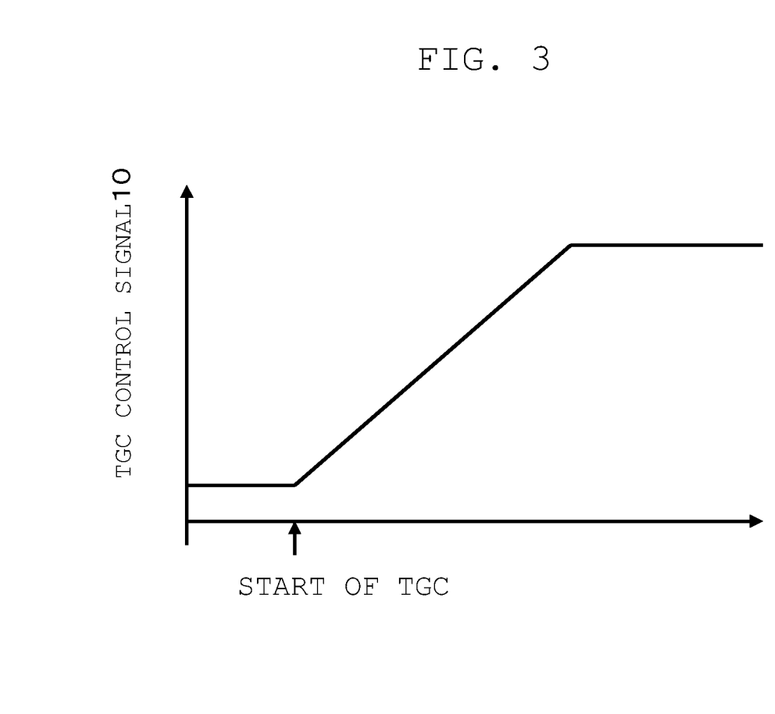
FIG. 3 is a graph showing a temporal change of a TGC control signal 10 received by the probe according to the first embodiment from a main body of an ultrasound diagnostic apparatus.

The TGC control signal 10 is, for example, a ramp-up signal that gradually rises from the start of the time gain control (TGC) as shown in FIG. 3.

In the TGC control signal generator 20, the TGC control signal 10 is converted into a current by the voltage-current converter VIC21. Specifically, the voltage-current converter VIC21 converts the TGC control signal 10 into output currents 22 and 23 that gradually decrease from the start of the TGC.

The output current 23 flows into the MN21b, which is an N-channel MOSFET. The output current 22 is converted into an output current 22' whose polarity is converted by the current mirror CM21, and flows into the MP21a which is a P-channel MOSFET. Gate potentials of the MP21a and the MN21b become the attenuator control signal 30.

The generated one pair of attenuator control signals 30 are input to the control terminal (gate) of the MP301a, which is a P-channel MOSFET, and the control terminal (gate) of the MN301b, which is an N-channel MOSFET, of the variable attenuator 300.

As a result, the gate-source voltage of the MN301b gradually decreases from the start of the TGC, so that a drain-source resistance RMN gradually increases. Similarly, since a source-gate voltage of the MP301a gradually decreases from the start of the TGC, a drain-source resistance RMP also gradually increases.

The receive signal of the first signal line 500 is greatly attenuated at the start of the time gain control (TGC) (at the receiving of the receive signal from the vicinity of the body surface) in which the resistances of the MP301a and the MN301b are small, and the attenuation rate decreases as the resistances of the MP301a and the MN301b gradually increase (as the depth increases).

The attenuated receive signal is input to the amplifier 400.

The LNA 402 of the amplifier 400 amplifies the received signal while minimizing an influence of deterioration of a signal-to-noise ratio. The LNA 402 operates with the power supply VDD2. Although also depending on the circuit configuration, the LNA 402 is configured to amplify a signal oscillating around a predetermined bias voltage VDCIN between the voltage of the power supply VDD2 and a ground level voltage.

The potential (bias voltage) VDC of the first signal line 500 is determined by the bias current Ibias and the resistance value of the resistor R205 as described above, and is different from the bias voltage VDCIN of the LNA 402.

Therefore, the first capacitor 401 is disposed in front of the LNA 402, such that a bias voltage of a terminal 501 of the first capacitor 401 on the LNA 402 side matches the bias voltage VDCIN of the LNA 402 and is connected to the LNA 402.

Principle of Implementing TGC by Variable Attenuator 300

The principle by which the time gain control is implemented by the variable attenuator 300 will be described in more detail using mathematical expressions.

Assuming that the impedance of the ultrasound transducer 100 is $Z_{TD}$, the ON resistance of the transmit/receive switch 200 is $R_{TRSWON}$, the drain-source resistances of the MN301$b$ and the MP301$a$ of the variable attenuator 300 are $R_{DSN301b}$ and $R_{DSP301a}$, the capacitance of the second capacitor 40 is $C_{40}$, the impedance of the second capacitor 40 is $Z_{40}$, and the resistance of the variable attenuator 300 is $R_{ATT}$, a current $I_{ATT}$ flowing through the variable attenuator 300 is obtained by Expression (3) using Expression (1) and Expression (2).

$$Z_{40}=j/(2\pi f \times C_{40}) \quad (1)$$

$$R_{ATT}=R_{DSN301b} \times R_{DSPa301}/(R_{DSN301b}+R_{DSP301a}) \quad (2)$$

$$I_{ATT}=|(R_{ATT}+Z_{40})/(Z_{TD}+R_{TRSWON}+R_{ATT}+Z_{40})| \quad (3)$$

In Expression (1), f represents a frequency, and j represents an imaginary unit (that is, $\sqrt{(-1)}$).

In particular, when an absolute value of the impedance $Z_{40}$ of the second capacitor 40 is sufficiently smaller than the resistance $R_{ATT}$ of the variable attenuator 300 ($|Z_{40}| \ll R_{ATT}$) within a desired band of the receive signal, the current $I_{ATT}$ flowing through the variable attenuator 300 is expressed by Expression (4).

$$I_{ATT} \approx |(R_{ATT})/(Z_{TD}+R_{TRSWON}+R_{ATT})| \quad (4)$$

Assuming that the input impedance of the amplifier 400 is sufficiently large, the receive signal converted from the ultrasound wave into the electric signal by the ultrasound transducer 100 is attenuated by the attenuation degree of $|20 \times \log(I_{ATT})|$[dB], and is input to the amplifier 400.

Figure 4:
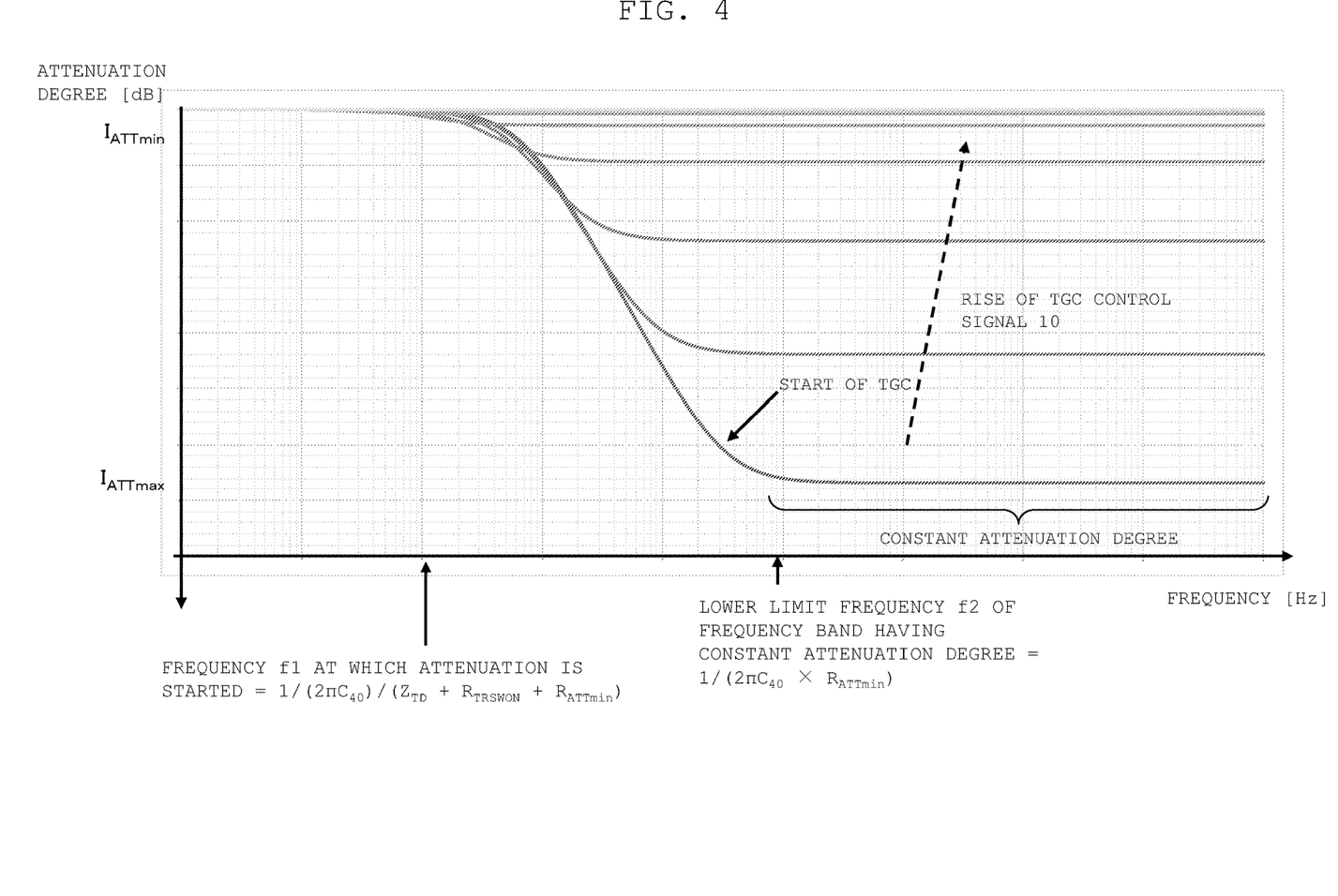
FIG. 4 is a graph showing a frequency-to-attenuation degree characteristic of a variable attenuator 300 of the probe according to the first embodiment.

Here, the drain-source resistances $R_{DSN301b}$ and $R_{DSP301a}$ of the MN301$b$ and the MP301$a$ of the variable attenuator 300 are functions of the attenuator control signal 30. The attenuator control signal 30 is a function of the TGC control signal 10, and the TGC control signal 10 is a signal that rises with time as shown in FIG. 3. Therefore, the attenuation degree of an amplitude of a signal input to the amplifier 400 decreases with time as shown in FIG. 4. As a result, the signal at the start of the time gain control (the receive signal from near the body surface) can be attenuated the most, and can be attenuated while reducing the attenuation degree in accordance with the passage of time. That is, a gain of the receive circuit can be controlled with time gain.

Design of Value of Electrostatic Capacitance $C_{40}$ of Second Capacitor 40

The design of the value of the electrostatic capacitance $C_{40}$ of the second capacitor 40 will be described using mathematical expressions.

Assuming that a minimum value and a maximum value of the resistor $R_{ATT}$ of the variable attenuator 300 that can be set by the attenuator control signal 30 are $R_{ATTmin}$ and $R_{ATTmax}$, respectively, and a minimum value (a value that minimizes a receive gain) and a maximum value (a value that maximizes the receive gain) of the current $I_{ATT}$ flowing through the variable attenuator 300 are $I_{ATTmax}$ and $I_{ATTMin}$, respectively, $I_{ATTmax}$ and $I_{ATTmin}$ are expressed by Expressions (5) and (6).

$$I_{ATTmax}=|(R_{ATTmin}+Z_{40})/(Z_{TD}+R_{TRSWON}+R_{ATTmin}+Z_{40})| \quad (5)$$

$$I_{ATTmin}=|(R_{ATTmax}+Z_{40})/(Z_{TD}+R_{TRSWON}+R_{ATTmax}+Z_{40})| \quad (6)$$

Therefore, a control range of the current $I_{ATT}$ flowing through the variable attenuator 300 is a range of Expression (7).

$$I_{ATTmax} \leq I_{ATT} \leq I_{ATTmin} \quad (7)$$

FIG. 4 shows a frequency-to-attenuation degree characteristic of the variable attenuator 300. As shown in FIG. 4, at the start of the TGC, the variable attenuator 300 starts attenuation at a frequency f1, and the attenuation degree becomes constant in a band having a frequency equal to or higher than a frequency f2. The frequency f1 and the frequency f2 are expressed by Expressions (8) and (9).

$$\text{Frequency } f1=1/(2\pi C_{40})/(Z_{TD}+R_{TRSWON}+R_{ATTmin}) \quad (8)$$

$$\text{Frequency } f2=1/(2\pi C_{40} \times R_{ATTmin}) \quad (9)$$

Therefore, the capacitance $C_{40}$, the $R_{TRSWON}$, and the $R_{ATTmin}$ of the second capacitor 40 are designed such that at least the frequency band of the receive signal used for generating an ultrasound image is included in a higher frequency band than the frequency f2 at which the attenuation degree is constant. For example, by adjusting the capacitance $C_{40}$ of the second capacitor 40, the frequency band of the receive signal used for generating the ultrasound image can be made larger than the frequency f2 relatively easily.

By making the resistance RAT T of the variable attenuator 300 sufficiently smaller than the impedance $Z_{40}$ of the second capacitor 40 ($R_{ATT} \ll Z_{40}$), a variable range of the drain-source resistances of the MN301 and the PN301 used as voltage control variable resistors can be more effectively utilized.

According to the present embodiment, the second capacitor 40 is a separate element from the 2D array IC 50 and is connected to the 2D array IC 50 via the pad 41, but the second capacitor 40 may be mounted on the 2D array IC 50. In a case where the control range of the current $I_{ATT}$ flowing through the variable attenuator 300 can ensure an area in which the second capacitor 40 can be formed in a range satisfying use, the second capacitor 40 may be mounted in the same die area as the M×N transmit and receive circuits mounted on the 2D array IC 50 and block circuits around the transmit and receive circuits.

As described above, according to the first embodiment, since the M×N transmit and receive channels ECh11 to EChMN are mounted in a matrix on the same 2D array IC 50, and one TGC control signal generator 20 may disposed around the transmit and receive channels with a high degree of freedom, it is possible to prevent an increase in a size of a circuit mounted on the 2D array IC 50.

According to the present embodiment, it is possible to connect one independent receive circuit 700 having a gain variable function with small variation to each of the ultrasound transducers 100 of several thousands to ten thousands of elements.

A large number of the ultrasound transducers 100 are arranged in a 2D array, and time gain control can be executed while preventing the size of the circuit and power consumption.

Therefore, it is possible to provide the ultrasound diagnostic apparatus including a 2D array probe in which an SNR of a diagnostic image is improved in both the vicinity and the deep portion of the body surface.

The 2D array IC 50 mounted in the probe can generate the attenuator control signal 30 for controlling the gain of the variable attenuator 300 by itself. As a result, it is possible to simultaneously control the gains of a large number of amplifiers 400. Therefore, it is possible to prevent a variation in the gains of a large number of transmit and receive channels Echs, and to form a TGC circuit suitable for the 2D array IC 50.

Since the bypass signal line 206 is arranged such that the bias current Ibias flows through the resistor R205 even when the transmit/receive switch 200 is turned off, the potential (bias voltage) VDC of the first signal line 500 can be kept constant both when the transmit/receive switch 200 is turned on and turned off. As a result, the bias potential of the receive signal input to the LNA 402 of the amplifier 400 can be kept constant, and amplification processing of the LNA 402 can be stabilized.

Second Embodiment

Figure 5:
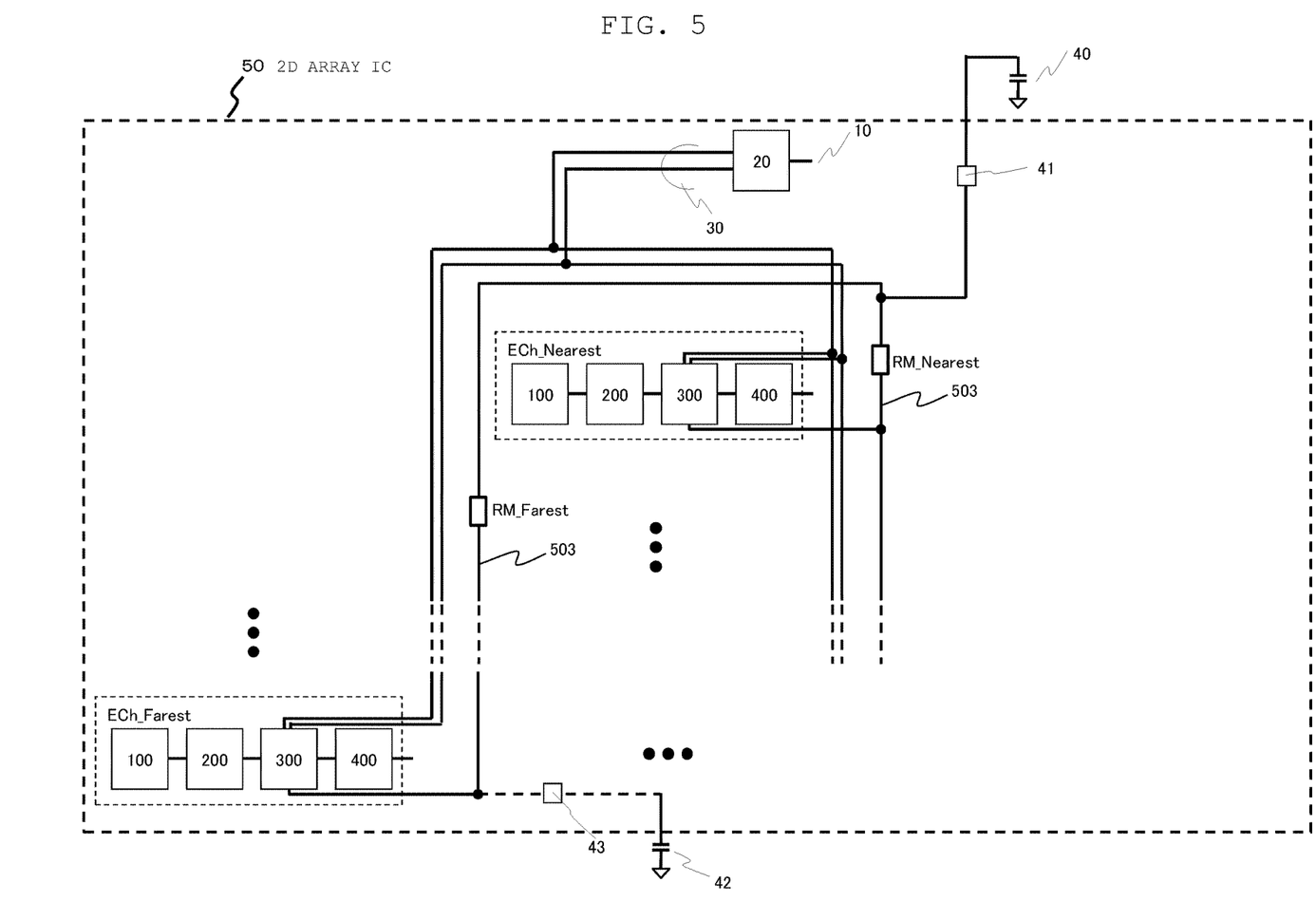
FIG. 5 is a block diagram showing an outline of an integrated circuit (a 2D array IC 50) in which a plurality of transmit and receive circuits (transmit and receive channels ECHs) are mounted, in a probe according to a second embodiment.

A probe for an ultrasound diagnostic apparatus according to a second embodiment will be described with reference to FIG. 5. FIG. 5 is a diagram showing an outline of a circuit of a 2D array IC 50 in which a plurality of transmit and receive circuits in the probe are mounted.

The 2D array IC 50 according to the second embodiment has a configuration in which the transmit and receive channels ECh11 to EChMN are two-dimensionally arranged as in the first embodiment, but a third capacitor 42 is further added as a common capacitor in addition to the second capacitor 40. The transmit and receive channel ECh distant from the second capacitor 40 and the pad 41 is connected to a pad 43 connected to the third capacitor 42. That is, each of the transmit and receive channels ECh11 to EChMN is connected to a pad, among two or more pads 41 and 43, which is at a position nearest to the transmit and receive channel ECh such that a length of a wiring line connected to the second capacitor 40 or the third capacitor 42 is equal to or less than a predetermined value. As a result, a wiring line 503 connecting the transmit and receive channel ECh and the second capacitor 40 or the third capacitor 42 is shortened, and a wiring resistance is added to the resistance of the variable attenuator 300, thereby preventing a change in the attenuation degree.

This will be further described using mathematical expressions. In FIG. 5, the same components as those in FIGS. 1 to 4 are denoted by the same reference numerals, and the descriptions thereof will be omitted.

In FIG. 5, a wiring resistance of the wiring line 503 from a transmit and receive channel ECh$_{\_Nearest}$ nearest to the second capacitor 40 to the second capacitor 40 is represented by R$_{M\_Nearest}$ and a wiring resistance of the wiring line 503 from a transmit and receive channel ECh$_{\_Farest}$ farthest to the second capacitor 40 to the second capacitor 40 is represented by R$_{M\_Farest}$.

Since a large number (M×N) of transmit and receive circuits are mounted on the 2D array IC 50, the current I$_{ATT}$ flowing through the variable attenuator 300 differs between the transmit and receive channel ECh$_{\_Nearest}$ nearest to the second capacitor 40 and the transmit and receive channel ECh$_{\_Farest}$ farthest from the second capacitor 40 due to the difference between the wiring resistance R$_{M\_Nearest}$ and the wiring resistance R$_{M\_Farest}$. At this time, maximum values and minimum values of the currents I$_{ATT}$ flowing through the variable attenuators 300 of the transmit and receive channel ECh$_{\_Nearest}$ and the transmit and receive channel ECh Farest are referred to as I$_{ATT\_Nearest\_max}$ and I$_{ATT\_Nearest\_min}$, and I$_{ATT\_Farest\_max}$ and I$_{ATT\_Farest\_min}$, respectively. By adding the wiring resistances R$_{M\_Nearest}$ and R$_{M\_Farest}$ to Expressions (5) and (6), these values are expressed by Expressions (10) to (13), respectively.

$$I_{ATT\_Nearest\_max}=|(R_{ATTmin}+Z_{40}+R_{M\_Nearest})/(Z_{TD}+R_{TRSWON}+R_{ATTmin}+Z_{40}+R_{M\_Nearest})| \quad (10)$$

$$I_{ATT\_Nearest\_min}=|(R_{ATTmax}+Z_{40}+R_{M\_Nearest})/(Z_{TD}+R_{TRSWON}+R_{ATTmax}+Z_{40}+R_{M\_Nearest})| \quad (11)$$

$$I_{ATT\_Farest\_max}=|(R_{ATTmin}+Z_{40}+R_{M\_Farest})/(Z_{TD}+R_{TRSWON}+R_{ATTmin}+Z_{40}+R_{M\_Farest})| \quad (12)$$

$$I_{ATT\_Farest\_min}=|(R_{ATTmax}+Z_{40}+R_{M\_Farest})/(Z_{TD}+R_{TRSWON}+R_{ATTmax}+Z_{40}+R_{M\_Farest})| \quad (13)$$

In Expressions (10) to (13), R$_{ATTmin}$ and R$_{ATTmax}$ represent the minimum value and the maximum value of the resistance R$_{ATT}$ of the variable attenuator 300, respectively, Z$_{40}$ represents the impedance of the second capacitor 40, Z$_{TD}$ represents the impedance of the ultrasound transducer 100, and R$_{TRSWON}$ represents the ON resistance of the transmit/receive switch 200.

Therefore, control ranges of the currents I$_{ATT\_Nearest}$ and I$_{ATT\_Farest}$ flowing through the variable attenuator 300 are ranges of Expressions (14) and (15).

$$I_{ATT\_Nearest\_max} \leq I_{ATT\_Nearest} \leq I_{ATT\_Nearest\_min} \quad (14)$$

$$I_{ATT\_Farest\_max} \leq I_{ATT\_Farest} \leq I_{ATT\_Farest\_min} \quad (15)$$

Since a large receive gain is required for the variable attenuator 300 at the end of the time gain control, the resistance R$_{ATTmax}$ of the variable attenuator 300 satisfies Expression (16).

$$R_{ATTmax} >> Z_{TD}+R_{TRSWON}+Z_{40}+\text{Wiring Resistance} \quad (16)$$

In this case, the minimum value current I$_{ATT\_Nearest\_min}$ of the current I$_{ATT}$ flowing through the variable attenuator 300 of the transmit and receive channel ECh$_{\_Nearest}$ nearest to the second capacitor 40 and the minimum value current I$_{ATT\_Farest\_min}$ of the current I$_{ATT}$ flowing through the variable attenuator 300 of the transmit and receive channel ECh$_{\_Farest}$ farthest from the second capacitor 40 can be approximated to be substantially equal to each other as in Expression (17).

$$I_{ATT\_Nearest\_min} \approx I_{ATT\_Farest\_min} \quad (17)$$

A difference between an attenuation degree in the variable attenuator 300 of the transmit and receive channel ECh$_{\_Nearest}$ nearest to the second capacitor 40 and an attenuation degree in the variable attenuator 300 of the transmit and receive channel ECh$_{\_Farest}$ farthest from the second capacitor 40 is represented by Expression (18).

$$|20 \log(I_{ATT\_Nearest} \max / I_{ATT\_Farest} \max)|[dB] \quad (18)$$

Therefore, when a specification in which the difference between the attenuation degrees represented by Expression (18) is, for example, within 1 dB is provided, some of the transmit and receive channels EChs located far from the second capacitor 40 have a small signal attenuation degree that does not satisfy the above-mentioned specification within 1 dB.

According to the present embodiment, as shown in FIG. 5, since the third capacitor 42 and the pad 43 are added in the vicinity of the transmit and receive channel $ECh_{Farest}$ farthest from the second capacitor 40, a decrease in the signal attenuation degree of the variable attenuator 300 can be prevented.

Accordingly, the variable attenuators 300 of a large number (M×N) of transmit and receive channels ECHs can prevent variation in the signal attenuation degree and execute uniform time gain control. Therefore, it is possible to provide the ultrasound diagnostic apparatus including the 2D array probe in which the SNR of both diagnostic images in the vicinity and the deep portion is improved.

Third Embodiment

Figure 6:
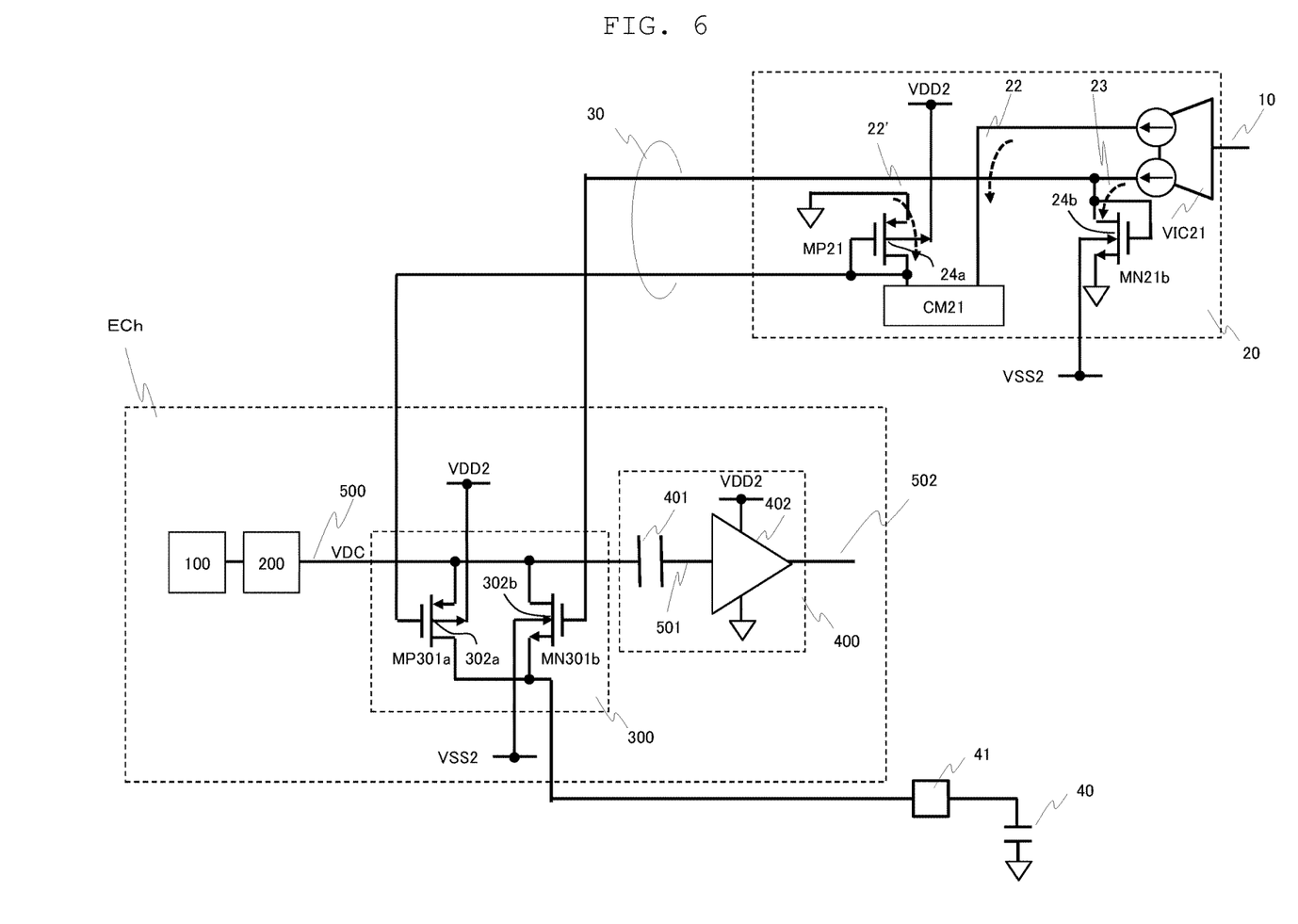
FIG. 6 is a block diagram showing a configuration of one transmit and receive circuit (a transmit and receive channel ECh) in a probe according to a third embodiment.

A probe for an ultrasound diagnostic apparatus according to a third embodiment will be described with reference to FIG. 6. FIG. 6 is a detailed diagram of a transmit and receive channel ECh according to the third embodiment. In FIG. 6, the same components as those in FIG. 2 are denoted by the same reference numerals, and the descriptions thereof will be omitted.

As described in the first embodiment, the receive signal converted from the ultrasound wave into the electric signal by the ultrasound transducer 100 oscillates around the potential (bias voltage) VDC of the first signal line 500. The potential VDC is a potential near the ground. Due to a signal oscillating with a large amplitude around this potential, the drain potential of the MN301b, which is an N-channel MOSFET, may be lower than the source potential. At this time, if a back gate 302b is connected to the ground, a current flows from the back gate 302b to a drain, and as a result, the signal of the first signal line 500 is distorted.

Therefore, according to the third embodiment, the back gate 302b of the MN301b is connected to a power supply VSS2 having a potential lower than that of the ground, thereby preventing a phenomenon of a current flowing from the back gate 302b to the drain. Accordingly, it is possible to prevent the signal of the first signal line 500 from being distorted.

Similarly, a back gate 302a of the MP301a, which is a P-channel MOSFET, is connected to a power supply VDD2 having a potential higher than that of the ground.

A back gate 24b of the MN21b, which is an N-channel MOSFET of the TGC control signal generator 20, is connected to the power supply VSS2. A back gate 24a of the MP21a, which is a P-channel MOSFET, is connected to the power supply VDD2.

Figure 7A:
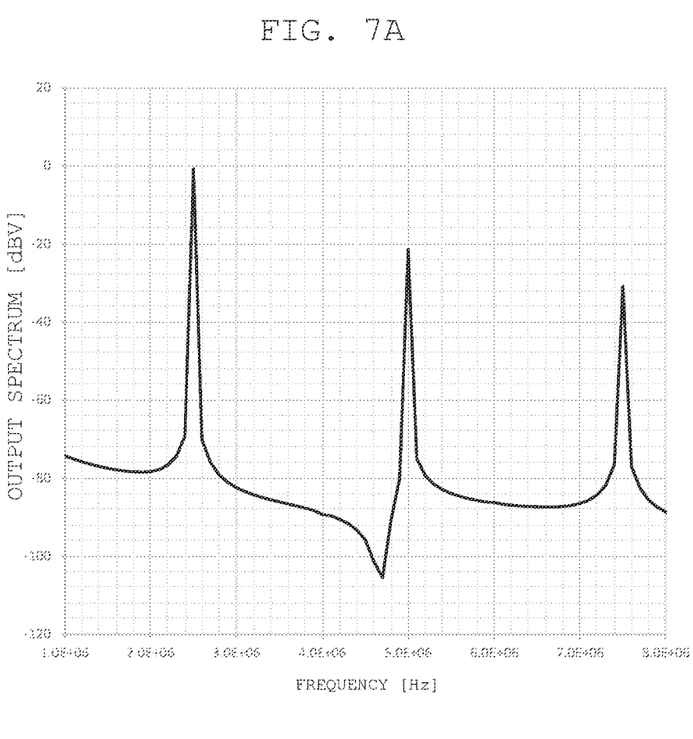
FIGS. 7A and 7B are spectra of an output signal when a sine wave signal of 2.5 MHz is input to the variable attenuator 300 of FIG. 6 according to the third embodiment.
Figure 7B:
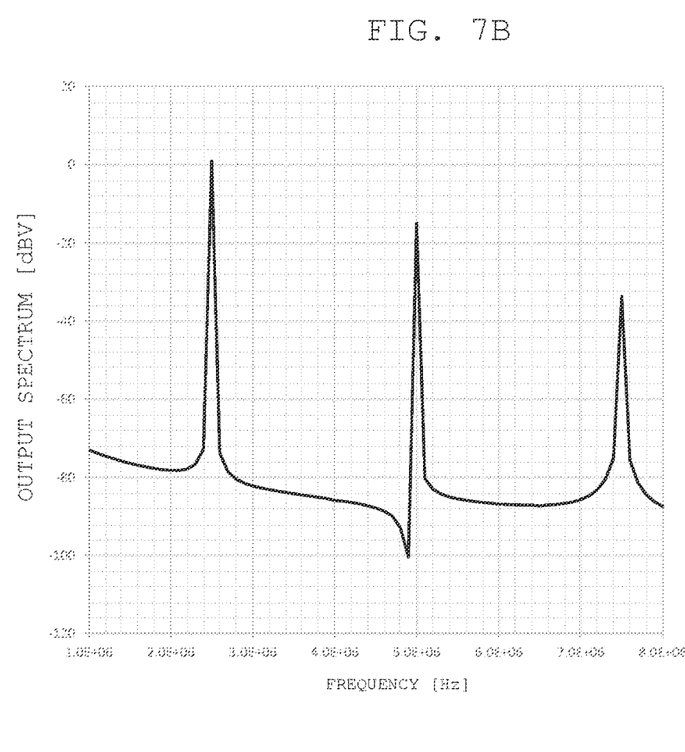

FIGS. 7A and 7B are spectra of output signals when a sine wave signal of 2.5 MHz is input to the variable attenuator 300 of FIG. 6. FIG. 7A shows the variable attenuator 300 in which the back gate 302b of the MN301b is connected to the power supply VSS2 and the back gate 302a of the MP301a is connected to the power supply VDDS as shown in FIG. 6, and FIG. 7B shows the variable attenuator 300 in which the back gates 302a and 302b are connected to the ground.

In the spectra of FIGS. 7A and 7B, the leftmost peak is a fundamental wave (here, a sine wave signal of 2.5 Hz), and the middle is a peak of a second harmonic wave. It is confirmed that a second harmonic wave level is more prevented in FIG. 7A than in FIG. 7B.

A configuration, an operation, and effects of a probe other than those described above are the same as those of the first embodiment.

Fourth Embodiment

Figure 8:
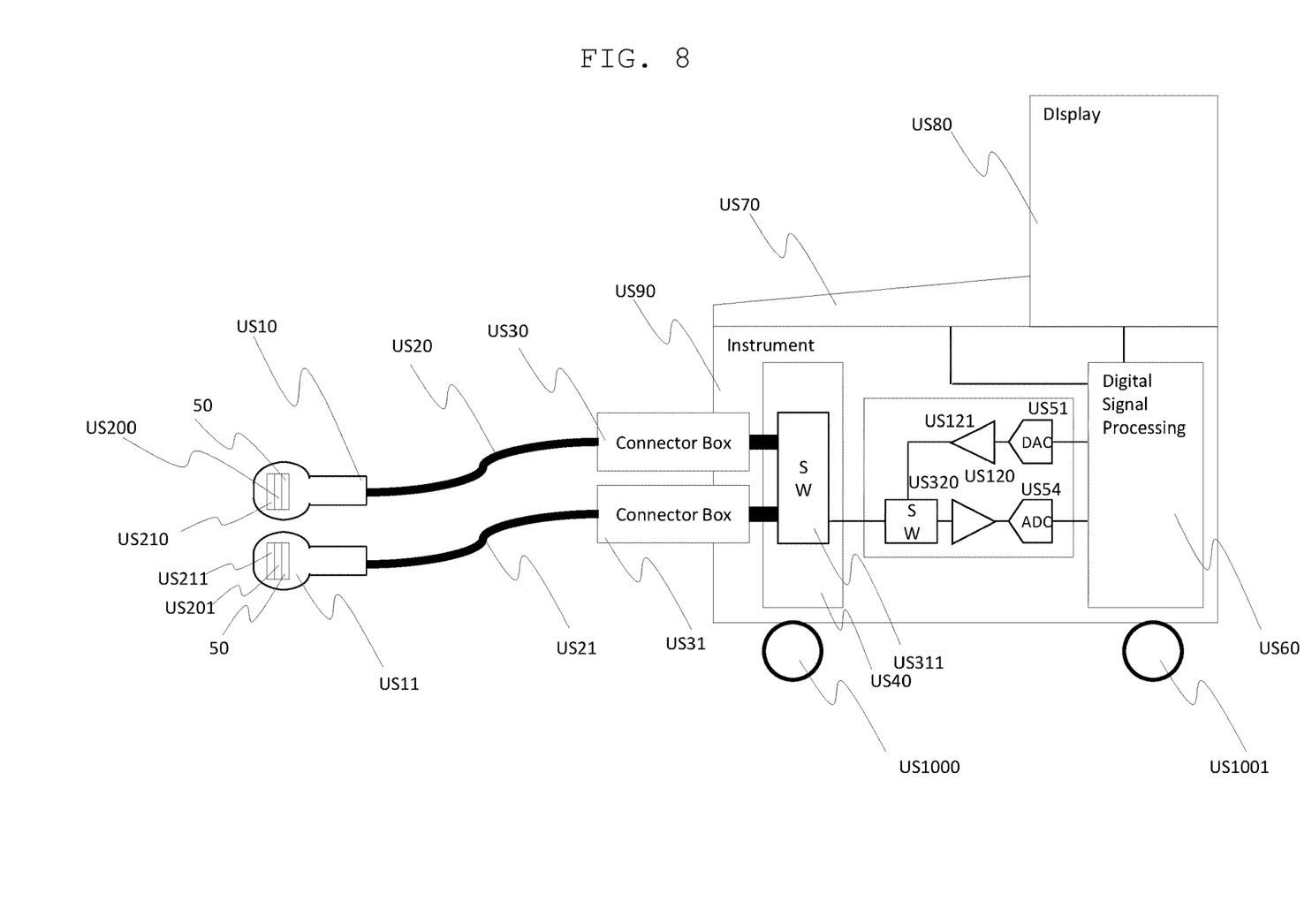
FIG. 8 is a block diagram showing a configuration of an ultrasound diagnostic apparatus according to a fourth embodiment.

FIG. 8 is a configuration diagram of an ultrasound diagnostic apparatus according to a fourth embodiment.

The ultrasound diagnostic apparatus includes: a main body device US90; a display US80; and an operation panel US70.

The main body device US90 is provided with connector boxes US30 and US31 to which probes are connected, and a probe selector US40.

A transmit/receive switch US320, an amplifier US121, an amplifier US120, an analog-to-digital converter US54, and a signal processing circuit US60 are arranged in the main body device US90. On a bottom surface of the main body device US90, casters US1000 and US1001 are provided, and the ultrasound diagnostic apparatus is freely movable on a floor surface field.

The amplifier US121 amplifies the transmit signal. The transmit/receive switch US320 serves to prevent the transmit signal from going around to a receive system. The amplifier US120 amplifies receive signals of sub channels received from probes US10 and US11.

The signal processing circuit US60 is a logic circuit, receives an output signal of the amplifier US120 as a digital signal via the analog-to-digital converter US54, and performs signal processing to generate an ultrasound image. At the time of transmitting, the signal processing circuit US60 inputs the transmit signal subjected to the signal processing to the amplifier US121 via a digital-to-analog converter US51, and transmits the transmit signal to 2D array probes US10 and US11 via the probe selector US40, the connector boxes US30 and US31, and cables US20 and US21.

The probes US10 and US11 are connected to the connector boxes US30 and US31 via the cables US20 and US21, respectively. The probe selector US40 selectively connects one of the probes US10 and US11 to the transmit/receive switch US320.

The 2D array IC 50 according to any of the first to third embodiments is mounted in each of the probes US10 and US11. Matching layers US200 and US201 are also arranged in the probes US10 and US11, and acoustic lenses US210 and US211 are also arranged in the probes US10 and US11, respectively. The matching layers US200 and US201 match the ultrasound transducer 100 of the 2D array with acoustic impedances of a living body. The acoustic lens US210 converges an ultrasound beam.

The main body device US90 of the ultrasound diagnostic apparatus in FIG. 8 includes two connector boxes US30 and US31, and two 2D array probes US10 and US11 are connected to the connector boxes US30 and US31, but the number of connected probes is not limited to two. A 1D array probe or the like in the related art can also be connected to the connector boxes US30 and US31. Further, a connector box connection terminal for connecting a special probe such as a Doppler probe may be provided.

Various operations of the main body device US90, such as which site in a body of a patient is viewed, are executed by the operation panel US70. The main body device US90 includes various diagnosis modes, and switching of the diagnosis modes is also executed by the operation panel US70. The diagnosis modes includes: a brightness (B) mode; a pulsed wave doppler (PW) mode; a color flow mapping (CFM) mode; and a steerable CW doppler (STCW) mode.

The B mode is a mode in which a receive amplitude intensity of an ultrasound wave reflected from a tissue is displayed in association with brightness.

The PW mode is a mode in which an ultrasound wave is repeatedly transmitted toward a certain depth, and every time the signal is repeatedly transmitted, a frequency shift of a signal reflected from this site is measured to obtain a blood flow velocity. In the PW mode, the blood flow velocity at a specific position can be known, and can be displayed so as to be superimposed on a B-mode image.

The CFM is also called a color doppler, and is a mode in which the blood flow velocity is visualized by obtaining an autocorrelation of a receive signal for each ultrasound wave transmitting. In the CFM mode, an average speed of positions at a large number of points on a receive beam of the ultrasound wave is known, and is used for finding a reverse flow or the like.

The STCW mode is also a mode for measuring the blood flow velocity, and this mode is suitable for fast blood flow velocity measurement.

The signal processing circuit US60 processes the signal from the analog-to-digital converter US54 to generate a diagnostic image of the above-mentioned various modes. The image is displayed on the display US80.

The TGC circuit according to the present embodiment is not limited to the 2D array IC, and can be used for receive of an ultrasound signal by a normal ultrasound probe such as a 1D probe. The same TGC function can be implemented even if the TGC function is mounted on the device side instead of the probe.

Although the embodiments have been described above, the invention is not limited to the above-mentioned embodiments, and includes various modifications. For example, the above-mentioned embodiments are described in detail for easy understanding of the invention, and the invention is not necessarily limited to those including all the configurations described above.

What is claimed is:

1. A probe that is connected to an ultrasound diagnostic apparatus, and is configured to transmit an ultrasound wave to a diagnostic site and receive a receive signal which is a reflected wave, the probe comprising:
   a plurality of receive circuits, wherein
   each of the receive circuits includes:
   an ultrasound transducer that is configured to convert the receive signal into a ground level electric signal and output the electric signal as a first output signal;
   a transmit/receive switch that is connected to a first signal line and is configured to switch depending on whether to output the first output signal output from the ultrasound transducer to the first signal line;
   a variable attenuator that is provided with a control terminal and two terminals, and is configured to change a resistance value between the two terminals other than the control terminal based on a control signal input to the control terminal;
   a first capacitor that is connected to the first signal line; and
   an amplifier that has an input terminal connected to the first capacitor and includes at least an amplifier circuit configured to amplify an electric signal of the first signal line and output the amplified electric signal to a second signal line,
   the transmit/receive switch is configured to output a bias potential to the first signal line when the transmit/receive switch is turned off, and
   in the variable attenuator, one terminal of the two terminals other than the control terminal is connected to the first signal line, and another terminal is connected to the ground via a second capacitor different from the first capacitor.

2. The probe according to claim 1, further comprising an integrated circuit and one or more common capacitors disposed outside the integrated circuit, wherein
   the integrated circuit includes a plurality of the receive circuits,
   the common capacitor is connected to the plurality of receive circuits and operates as the second capacitor of the plurality of receive circuits, and
   the common capacitor is located outside the integrated circuit.

3. The probe according to claim 2, wherein
   an electrostatic capacitance of the common capacitor is larger than an electrostatic capacitance of the first capacitor.

4. The probe according to claim 2, comprising:
   one or more control signal generators configured to output the control signal to each of the plurality of receive circuits, wherein
   the control signal generator is mounted in a region around a region where the plurality of receive circuits are mounted in the integrated circuit.

5. The probe according to claim 2, wherein
   two or more common capacitors are provided, and the common capacitors are respectively connected to the plurality of the receive circuits via two or more pads provided in the integrated circuit, and
   each receive circuit is connected to a pad, among the two or more pads, which is at a position nearest to the receive circuit such that a length of a wiring line connected to the common capacitor is equal to or less than a predetermined value.

6. The probe according to claim 1, wherein
   an OFF state bias potential output to the first signal line when the transmit/receive switch is turned off is equal to an ON state bias potential output to the first signal line when the transmit/receive switch is turned on.

7. The probe according to claim 1, wherein
   the transmit/receive switch includes one or more MOSFETs, and has a function of causing a current for determining the bias potential of the first signal line to flow to the first capacitor side without passing through a high-breakdown-voltage MOSFET when the transmit/receive switch is turned off.

8. The probe according to claim 1, wherein
   the variable attenuator includes one or more MOSFETs including the control terminal and the two terminals, and
   a back gate of the MOSFET is connected to a power supply that is not at a ground potential.

9. An ultrasound diagnostic apparatus comprising:
   the probe according to claim 1; and
   a processing device configured to process a signal received from the probe.

10. A probe that is connected to an ultrasound diagnostic apparatus, and is configured to transmit an ultrasound wave to a target site and receive an ultrasound signal which is a reflected wave, the probe comprising:
    a plurality of arranged ultrasound transducers; a plurality of transmit circuits configured to respectively output transmit signals to the plurality of ultrasound transducers; and a plurality of receive circuits respectively connected to the plurality of ultrasound transducers, wherein each of the plurality of receive circuits includes: a transmit/receive switch; an amplifier circuit; a first signal line connecting the transmit/receive switch to the amplifier circuit; and a variable attenuator connected to an intermediate portion of the first signal line, the ultrasound transducers convert the ultrasound signal into an electric signal and output the electric signal to the transmit/receive switch as a first output signal, the transmit/receive switch switches depending on whether to output the first output signal from the ultrasound transducer to the first signal line, and the variable attenuator includes one or more elements, the element is an element in which a control terminal and two terminals are provided and a resistance value changes between the two terminals other than the control terminal according to a control signal input to the control terminal, and one of the two terminals of the element is connected to the first signal line.

11. The probe according to claim 10, wherein
the one or more elements of the variable attenuator include an N-channel MOSFET and a P-channel MOSFET, the N-channel MOSFET and the P-channel MOSFET are connected in parallel, one terminal side of the parallel connected MOSFETs is connected to the first signal line, and another terminal side is connected to the ground via a second capacitor.

12. The probe according to claim 10, wherein
the transmit/receive switch includes: one or more transmit/receive switch MOSFETs; a floating voltage generation unit; a switch element; a bypass signal line; and a resistor having one end connected to the first signal line, one of a source terminal and a drain terminal of the transmit/receive switch MOSFET is connected to the ultrasound transducer, and another one of the source terminal and the drain terminal is connected to the first signal line, the floating voltage generation unit generates a voltage to be applied between a gate and a source of the transmit/receive switch MOSFET, the one end of the resistor is connected to the first signal line, and another end of the resistor is connected to the ground, and the switch element includes: a switch terminal connected to a bias current source; an ON terminal; and an OFF terminal, the ON terminal is connected to the floating voltage generation unit and supplies a bias current to the floating voltage generation unit when the switch element is turned on, and the OFF terminal is connected to the first signal line via the bypass signal line and causes the bias current to flow into the resistor via the first signal line when the switch element is turned off.

13. The probe according to claim 10, wherein
a first capacitor is inserted in series in the first signal line between the amplifier circuit and the transmit/receive switch.

14. An ultrasound diagnostic apparatus comprising:
the probe according to claim 10; and
a processing device configured to process a signal received from the probe.

* * * * *